(12) United States Patent  (10) Patent No.: US 7,871,403 B2
Ito et al.  (45) Date of Patent: Jan. 18, 2011

(54) MEDICAL SUPPORT CONTROL SYSTEM

(75) Inventors: Masaru Ito, Yokohama (JP); Koichi Tashiro, Sagamihara (JP)

(73) Assignee: Olympus Medical Systems Corp. (JP)

( * ) Notice: Subject to any disclaimer, the term of this patent is extended or adjusted under 35 U.S.C. 154(b) by 144 days.

(21) Appl. No.: 12/037,254

(22) Filed: Feb. 26, 2008

(65) Prior Publication Data

US 2009/0217165 A1   Aug. 27, 2009

(51) Int. Cl.
*A61B 17/00* (2006.01)
(52) U.S. Cl. .................. 606/1; 700/1; 715/700
(58) Field of Classification Search .......... 606/1; 600/101; 700/1, 83, 90; 715/700, 716, 719; 710/1–7
See application file for complete search history.

(56) References Cited

U.S. PATENT DOCUMENTS

| 2003/0093503 A1* | 5/2003 | Yamaki et al. .............. 709/220 |
| 2005/0284491 A1 | 12/2005 | Tashiro et al. |
| 2007/0078335 A1 | 4/2007 | Horn |

FOREIGN PATENT DOCUMENTS

| JP | 2002-530172 | 9/2002 |
| JP | 2006-536 | 1/2006 |
| JP | 2007-125373 | 5/2007 |
| WO | WO 00/31558 | 6/2000 |

* cited by examiner

*Primary Examiner*—Ahmed M Farah
(74) *Attorney, Agent, or Firm*—Ostrolenk Faber LLP

(57) ABSTRACT

A medical support control system comprising a recording device for recording an image signal from a medical device, a medical support control device for synthesizing an image based on the image signal and a prescribed GUI, and a display manipulation device for display the GUI, wherein: on the basis of an input of setting information about the recording device on an administrator setting window of a GUI displayed by the display manipulation device, the medical support control device creates a GUI including device selection means for causing one of the medical devices to be selected, image selection means for causing one of image signals output from the medical devices to be selected, and display means for causing the image corresponding to the selected image signal to be displayed, and causes the created GUI to be displayed on the display manipulation device as a manipulator window.

1 Claim, 10 Drawing Sheets

MEDICAL SUPPORT CONTROL SYSTEM

BACKGROUND OF THE INVENTION

1. Field of the Invention

The present invention relates to a medical support control system for controlling medical devices and non-medical devices used for operations.

2. Description of the Related Art

Operating systems using medical controllers or the like for controlling medical devices such as endoscopes or the like used for operations have been proposed. Medical devices to be controlled such as electric knives, insufflation devices, endoscope cameras, light source devices, or the like are connected to the medical controller (also referred to as an MC). Also, a display device, a manipulation panel, or the like is connected to the MC. The manipulation panel includes a display unit and a touch sensor, and is used as a central manipulation device by nurses, or the like working in an unsterilized area. The display device is used for displaying endoscope images or the like.

There is audio-visual equipment in the operating room, such as a room light, a room camera, an interphone device, a liquid crystal display device, or the like (non-medical devices). The audio-visual equipment is controlled independently or by a non-medical controller (also referred to as an NMC) used for the central control.

Japanese Patent Application Publication No. 2006-000536, for example, discloses an operating system, comprising:

a first controller connected to a medical device provided in an operating room;

a second controller connected to a non-medical device provided in the operating room; and manipulation instruction input means transmitting the content of a manipulation instruction to the first controller when a manipulation instruction for the medical device or the non-medical device is input. The first controller transmits to the second controller a first control signal in accordance with the manipulation instruction of the non-medical device input into the manipulation instruction means. The second controller converts the first control signal into a second control signal used for controlling the non-medical device, and transmits the second control signal to the non-medical device. Thereby, the operating system and a non-medical system work together, and the operating person himself/herself or the like can manipulate the non-medical devices.

SUMMARY OF THE INVENTION

The medical support control system according to the present invention is a system comprising:

a recording device for recording an image signal output from a medical device;

a medical support control device in which the image signal output from the medical device is input, the input image signal is recorded on the recording device, the image signal recorded on the recording device is input, and an image based on the image signal and a prescribed graphical user interface (GUI) are synthesized; and a display manipulation device in which the GUI containing the synthesized image is displayed and input is possible to the GUI, wherein:

on the basis of an input of setting information about the recording device on an administrator setting window of a GUI displayed by the display manipulation device, the medical support control device creates a GUI including device selection means for causing one of the medical devices to be selected, image selection means for causing one of image signals output from the medical devices to be selected, and display means for causing the image corresponding to the selected image signal to be displayed, and causes the created GUI to be displayed on the display manipulation device as a manipulator window.

DESCRIPTION OF THE PREFERRED EMBODIMENTS

Figure 1:
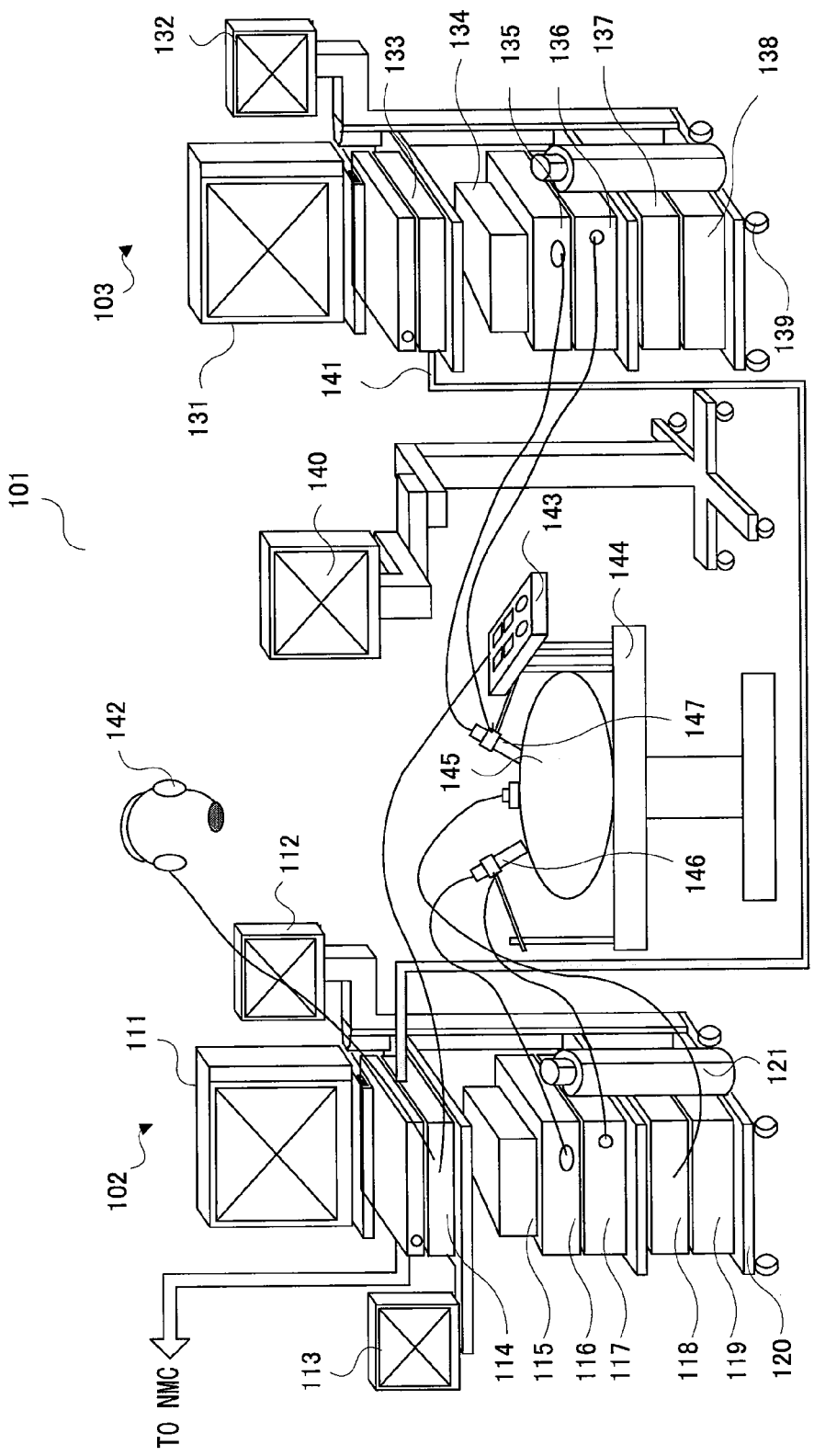
FIG. 1 shows an entire configuration of the medical device control system according to the present embodiment.

Hereinafter, the embodiments of the present invention will be explained in detail, referring to the drawings.

A medical support control system according to the present embodiment includes a medical device control system and a non-medical device control system. The medical device control system includes a plurality of medical devices and a medical controller for controlling these medical devices. The non-medical device control system includes non-medical devices (that may further include medical devices) that are used for operations, and a non-medical controller for controlling these non-medical devices.

An endoscopic operating system will be explained as an example of the medical device control system.

FIG. 1 shows an entire configuration of the medical device control system according to the present embodiment. An endoscopic operating system is shown as a medical device control system 101. In the operating room, a first endoscopic operating system 102 and a second endoscopic operating system 103 beside a bed 144 on which a patient 145 is laid and a wireless remote controller 143 for the operating person are provided.

The endoscopic operating systems 102 and 103 respectively have first and second trolleys 120 and 139 each including a plurality of endoscope peripheral devices used for observation, examination, procedures, recoding, and the like. Also, an endoscope image display panel 140 is arranged on a movable stand.

On the first trolley 120, an endoscope image display panel 111, a central display panel 112, a central manipulation panel device 113, a medical controller (MC) 114, a recorder 115, a video processor 116, an endoscope light source device 117, an insufflation unit 118, and an electrical surgical device 119 are arranged.

The central manipulation panel device 113 is arranged in an unsterilized area to be used by nurses or the like in order to manipulate the respective medical devices in a centralized manner. This central manipulation panel device 113 may include a pointing device such as a mouse, a touch panel, or the like (not shown). By using the central manipulation panel device 113, the medical devices can be managed, controlled, and manipulated in a centralized manner.

The respective medical devices are connected to the MC 114 via communication cables (not shown) such as serial interface cables or the like, and can have communications with one another.

Also, a headset-type microphone 142 can be connected to the MC 114. The MC 114 can recognize voices input through the headset-type microphone 142, and can control the respective devices in accordance with the voices of the operating person.

The endoscope light source device 117 is connected to a first endoscope 146 through a light-guide cable used for transmitting the illumination light. The illumination light emitted from the endoscope light source device 117 is provided to the light guide of the first endoscope 146 and illuminates the affected areas or the like in the abdomen of the patient 145 into which the insertion unit of the first endoscope 146 has been inserted.

The optical image data obtained through the camera head of the first endoscope 146 is transmitted to a video processor 116 through a camera cable. The optical image data undergoes signal processing in a signal processing circuit in the video processor 116, and the video signals are created.

The insufflation unit 118 provides $CO_2$ gas to the abdomen of the patient 145 through a tube. The $CO_2$ gas is obtained from a gas tank 121.

On the second trolley 139, an endoscope image display panel 131, a central display panel 132, a expansion unit 133, a recorder 134, a video processor 135, an endoscope light source device 136, and other medical devices 137 and 138 (such as an ultrasonic processing device, a lithotripsy device, a pump, a shaver, and the like) are arranged. These respective devices are connected to the expansion unit 133 through cables (not shown), and can communicate with one another. The MC 114 and the expansion unit 133 are connected to each other through the expansion cable 141.

The endoscope light source device 136 is connected to a second endoscope 147 through the light-guide cable for transmitting the illumination light. The illumination light emitted from the endoscope light source device 136 is provided to the light guide of the second endoscope 147, and illuminates the affected areas or the like in the abdomen of the patient 145 into which the insertion unit of the second endoscope 147 has been inserted.

The optical image data obtained through the camera head of the second endoscope 147 is transmitted to a video processor 135 through a camera cable. The optical image data undergoes signal processing in a signal processing circuit in the video processor 135, and the video signals are created. Then, the video signals are output to the endoscope image display panel 131, and endoscope images of the affected areas or the like are displayed on the endoscope image display panel 131.

Further, the MC 114 can be controlled by the operating person manipulating the devices in the unsterilized area. Also, the first and second trolleys 120 and 139 can include other devices such as printers, ultrasonic observation devices, or the like.

Figure 2:
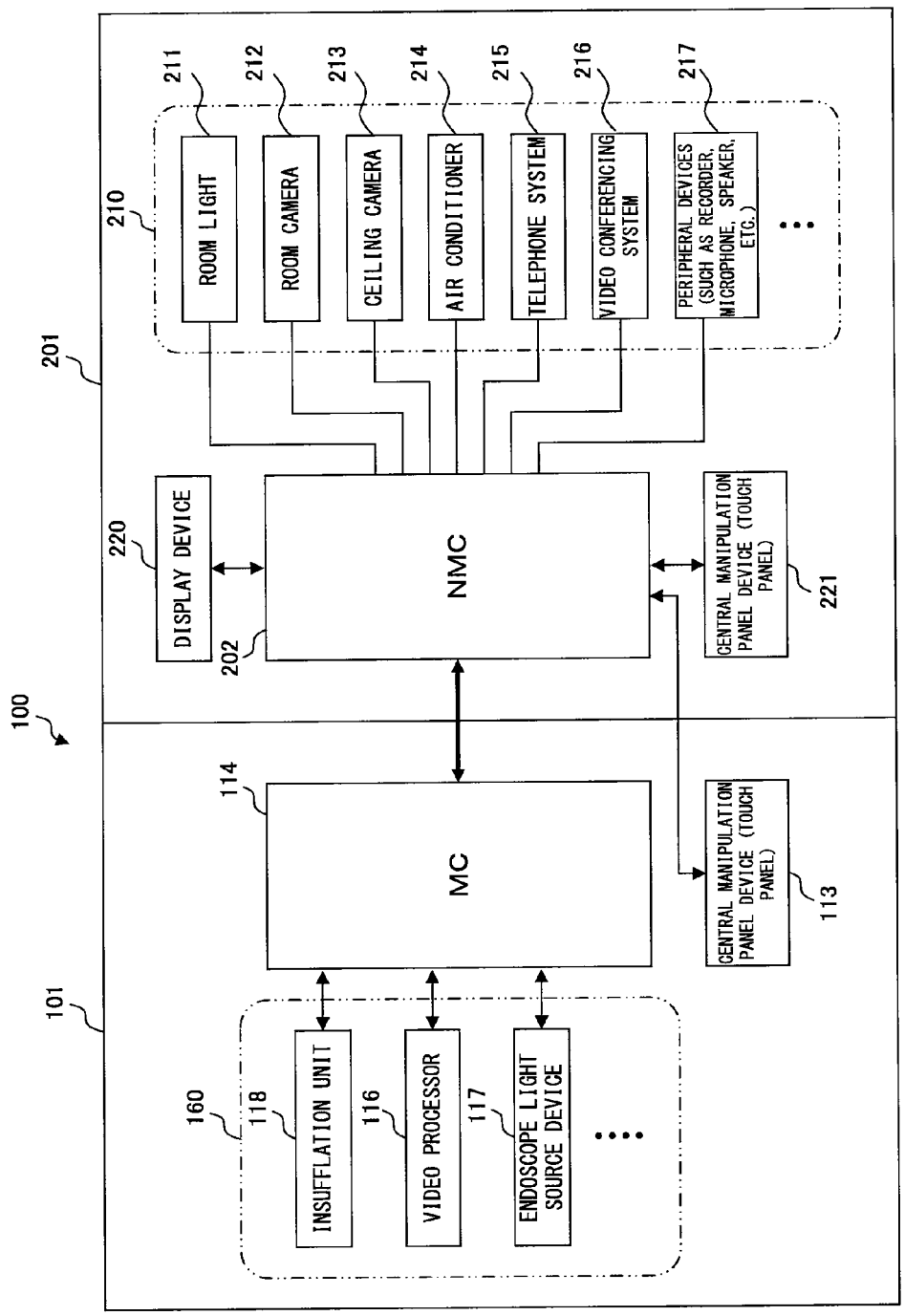
FIG. 2 is a block diagram showing an entire configuration of a medical support control system 100 according to the present embodiment.

FIG. 2 is a block diagram showing an entire configuration of a medical support control system 100 according to the present embodiment. As described above, the medical support control system 100 includes the medical device control system 101 and a non-medical device control system 201. A detailed configuration of the medical device control system 101 is as shown in FIG. 1. However, in FIG. 2, the medical device control system 101 is shown in a simplified manner for simplicity of explanation.

In FIG. 2, a medical device group 160 is a group of medical devices that are directly connected to the medical controller 114 or are indirectly connected to the MC 114 via the expansion unit 133. Examples of the devices included in the medical device group 160 are the insufflation unit 118, the video processor 116, the endoscope light source device 117, the electrical surgical device 119, and the like.

The central manipulation panel device 113 has a touch panel, and in accordance with the information input into the touch panel, the devices connected to the MC 114 or a non-medical device controller (NMC) 202 that will be described later can be manipulated.

The non-medical control system 201 includes the NMC 202 connected to the MC 114 through a communication cable or the like, and a non-medical device group 210. In this configuration, the NMC 202 can transmit and receive, through an image cable, the video signals to and from the medical device group 160 connected to the MC 114.

The NMC 202 controls the non-medical devices (including the audio-visual devices) connected thereto. As shown in FIG. 2, the non-medical device group 210 connected to the NMC 202 according to the present embodiment consists of a room light 211, a room camera 212, a ceiling camera 213, an air conditioner 214, a telephone system 215, a conference system 216 to be used for individuals in remote places (referred to as a video conference system hereinafter), and other peripheral devices 217. Further, a display device 220 and a central manipulation panel device 221 are connected to the NMC 202.

Also, the non-medical device group 210 includes equipment such as light devices provided in the operating room in addition to the AV devices used for recording and reproducing image data.

The display device 220 is a plasma display panel (PDP) or a liquid crystal display (LCD) device, and displays images of the predetermined device or images of the devices selected by nurses or the like through the central manipulation panel device 221. The room light 211 is a device that illuminates the operating room. The room camera 212 is used for shooting images of the situations in the operating room. The ceiling camera 213 is a camera suspended from the ceiling, whose positions can be changed. The conference system 216 is a system that displays images and transmits voices of nurses or the like in the medical office or the nurse stations, and enables conversations with them. The peripheral devices 217 are, for example, a printer, a CD player, a DVD recorder, and the like. The central manipulation panel device 221 has a touch panel that is the same as that included in the central manipulation panel device 113, and controls the respective AV devices connected to the NMC 202. The central manipulation panel devices 113 and 221 are referred to as TPs hereinafter.

Figure 3:
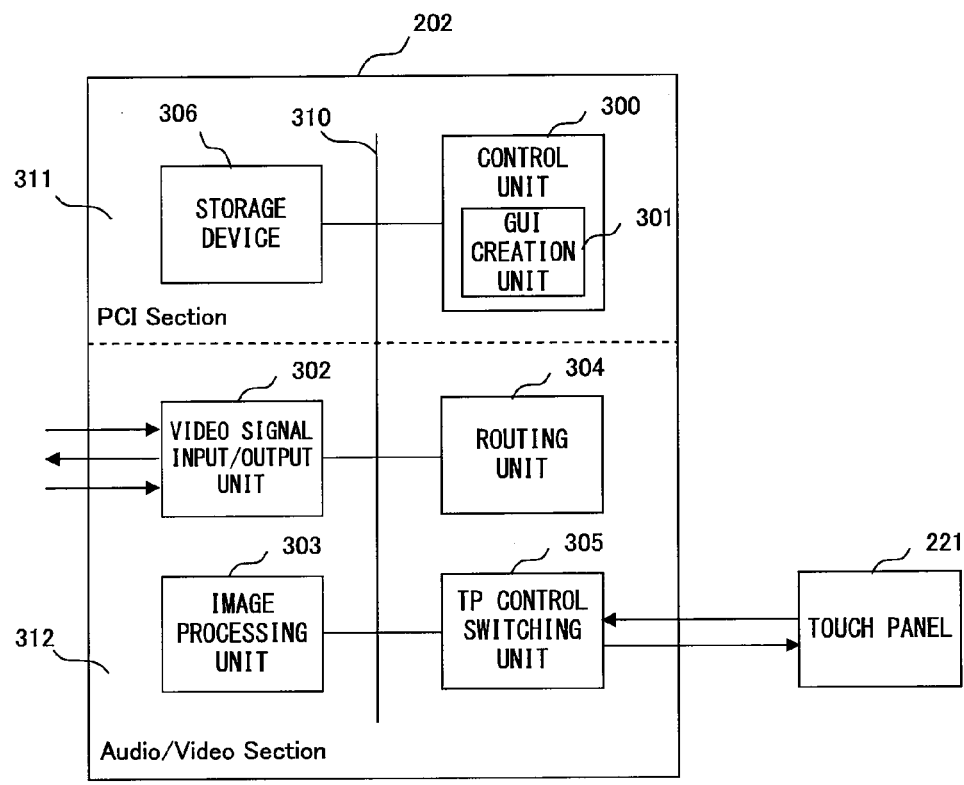
FIG. 3 is a block diagram showing a configuration of an NMC 202 in the present embodiment.

FIG. 3 is a block diagram showing a configuration of the NMC 202 in the present embodiment. The NMC 202 includes a PCI section 311 and an audio/video (A/V) section 312.

The PCI section 311 mainly controls a non-medical device group 210 connected to the NMC 202. The PCI section 311 includes a control unit 300 and a storage device 306. The control unit 300 controls the entirety of the PCI section 311, and transmits and receives data to and from the A/V section 312. The control unit 300 includes a GUI creation unit 301 and the like. Numeral 310 denotes a back plane.

The GUI creation unit 301 creates Graphical User Interface image information (hereinafter, referred to as GUI image information) that is an image layout to be displayed on a TP 221 or a monitor device, and transmits it to a routing unit 304.

The storage device 306 stores various programs, information set by the TP 221, and the like.

The A/V section 312 is a section that mainly processes the image signals and the audio signals. The A/V section 312 includes a video signal input/output unit 302, an image processing unit 303, a routing unit 304, and a TP control unit 305.

The video signal input/output unit 302 has a plurality of video signal input ports and a plurality of video signal output ports.

The routing unit 304 switches routes for the video signals input from the video signal input/output unit 302 and the video signals that were processed in the image processing unit 303, and transfers them to a prescribed configuration unit in the NMC 202. Also, the routing unit 304 transfers the GUI image information created in the GUI creation unit 301 to the TP control switching unit 305.

The image processing unit 303 performs image processing on the image information transferred from the routing unit 304. Examples of the image processing are the enlargement/reduction (scaling) of images, the mirroring of images, the rotation of images, displaying another, smaller image in a main image (picture in picture (PIP)), and displaying a plurality of images side by side (picture out picture (POP)).

The TP control switching unit 305 synthesizes the GUI image created in the GUI creation unit 301 with images created on the basis of the video signals transmitted from the video signal input/output unit 302. Then, the TP control switching unit 305 outputs the synthesized image to the TP 221. Also, the TP control unit 305 receives control signals (coordinate information) on the basis of touch manipulations from the TP 221, and transfers them to the control unit 300. Further, the TP control switching unit 305 can perform switching between the NMC 202 and the MC 114 as the manipulation targets of the TP 221.

Figure 4:
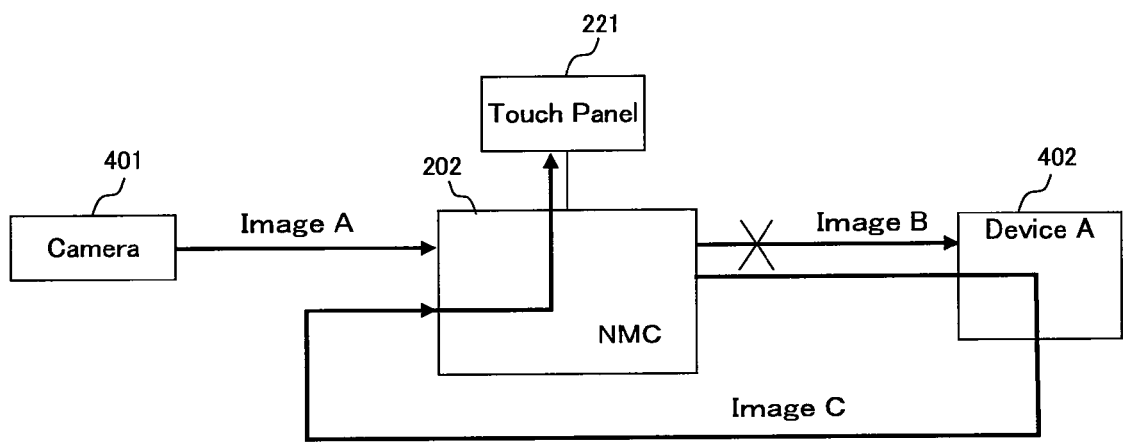
FIG. 4 shows the principle for performing a pre-view of video signals looped back to the NMC 202 according to the present embodiment.

FIG. 4 shows the principle for performing a preview of video signals looped back to the NMC 202 according to the present embodiment.

When, for example, image A obtained from a camera 401 is recorded on device A (402), image A that is the recording target is selected by using the TP 221, and device A (452) is selected as the output destination of image A (image B represents the image output from the NMC 202 to device A). In this case, the TP 221 performs a preview of image A for the confirmation of selection of image A.

When a cable between the NMC 202 and device A (402) is disconnected or when a connector thereof is removed, image B is not output to device A. However, a preview image of image A is displayed on the TP 221. This misleads the users into believing that image A in the preview image has been recorded on device A.

Accordingly, the image displayed on the preview area on the window displayed on the TP 221 is output via device A. In other words, when device A is selected as the recording destination of the video signals, an image returned from device A (image C) is designed to be automatically displayed as an image for the preview image to be displayed on the TP 221.

As will be explained by referring to the next figure, in the present embodiment, on the basis of the routing information set in advance, it is possible that the video signals input into the NMC 202 are output to a prescribed device and are recorded; thereafter the video signals are returned to the NMC 202 (in other words, the video signals are looped back), and are output to the TP 221.

Figure 5:
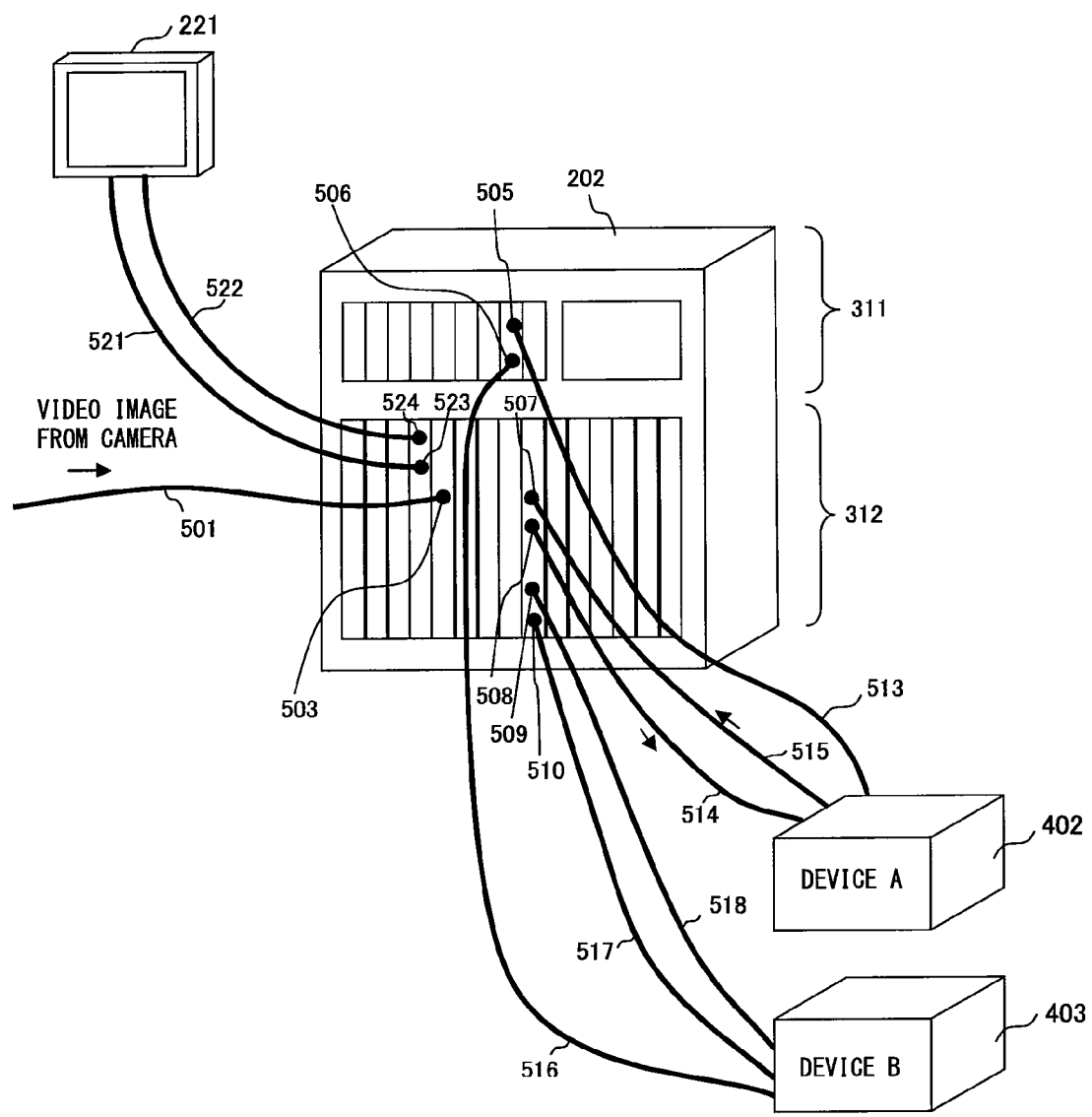
FIG. 5 shows an example of connection between the NMC 202 and a recorder for performing the pre-view of the video signals from the endoscope looped back from the recorder according to the present embodiment.

FIG. 5 shows an example of connection between the NMC 202 and the recorder for performing the preview of the video signals from the endoscope looped back from the recorder according to the present embodiment.

A video signal input port 503 of the NMC 202 is connected to the camera head of the endoscope via a communication cable 501. The video signals obtained through the endoscope are input into the video signal input port 503 via the communication cable 501.

Video signal output ports 508 and 510 of the NMC 202 and video signal output ports of device A (402) and device B (403) are respectively connected to each other via image cables 514 and 517. Video signal input ports 507 and 518 of the NMC 202 and video signal output ports of device A (402) and device B (403) are respectively connected via image cables 515 and 518. Also, communication ports 505 and 506 on the PCI section 311 side of the NMC 202 are respectively connected to communication ports of device A (402) and device B (403) via communication cables 513 and 516. Further, a plurality of devices may be connected.

Cables 521 and 522, which extend from the TP 221, are respectively connected to a TP output port 523 and a TP input port 524 of the NMC 202. The cable 521 is a cable for transmitting to the TP 221 images synthesized in the TP control unit 305. The cable 522 is a cable for transmitting to the TP control unit 305 the control signal based on touch manipulations on the TP 221.

Figure 6:
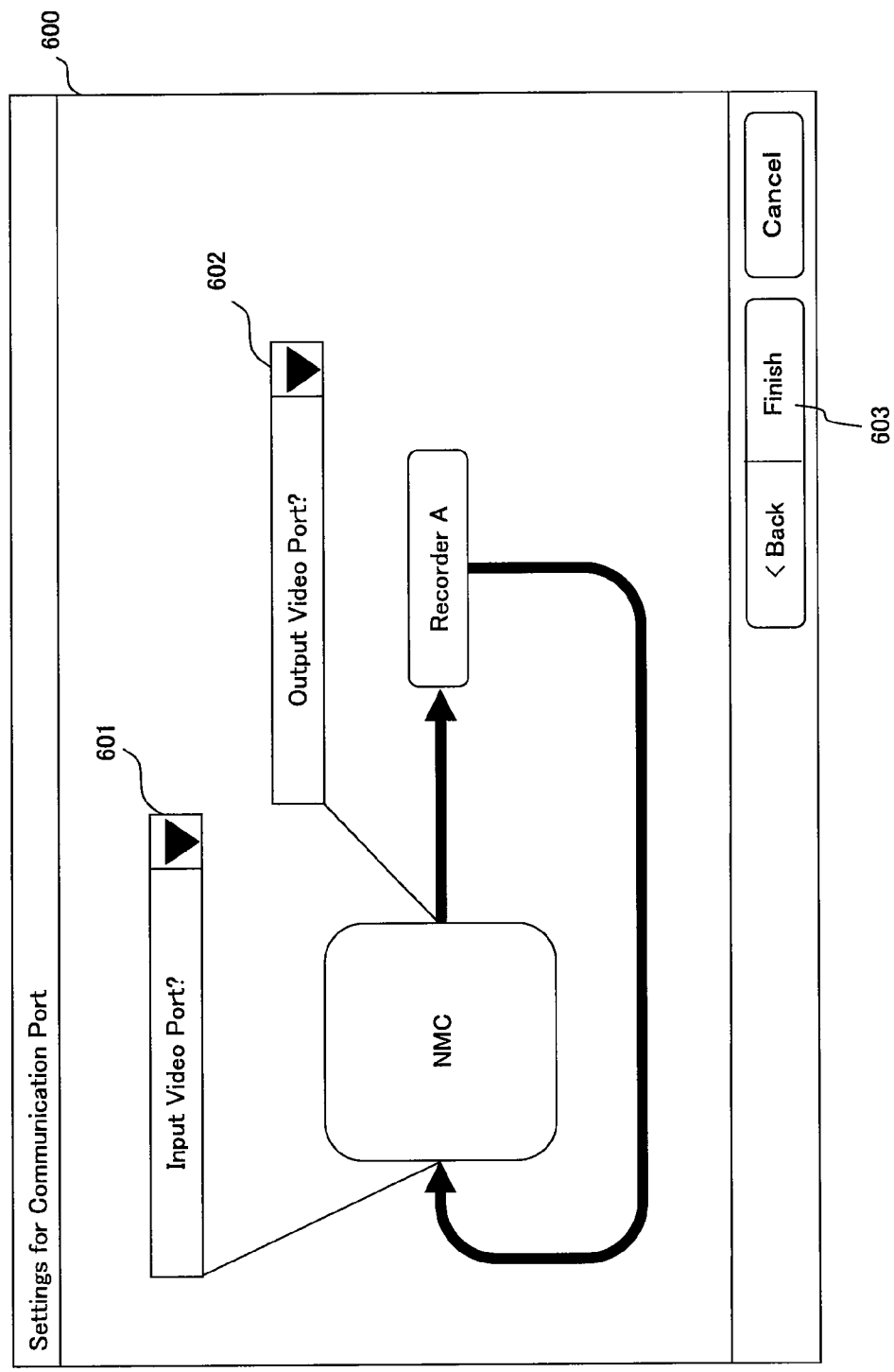
FIG. 6 shows a communication port setting window 600 for device A according to the present embodiment.

FIG. 6 shows a communication port setting window 600 for device A according to the present embodiment. The communication port setting window 600 is displayed on the TP 221 in the administrator mode. On the communication port setting window 600, it is possible to perform setting for the looping back of video signals for each device.

In an output video port setting unit 602, it is possible to set the output port on the NMC 202 side from which the video signals output to the device A. In FIG. 5, the video signal output port 508 is set in the output video port setting unit 602.

It is possible to set the input port on the NMC 202 side into which video signals output from device A are input. In FIG. 5, the video signal input port 507 is set in an input video port setting unit 601.

The information set in the communication port setting window 600 is registered in the storage device 306 when a "Finish" button 603 is pressed.

Figure 7:
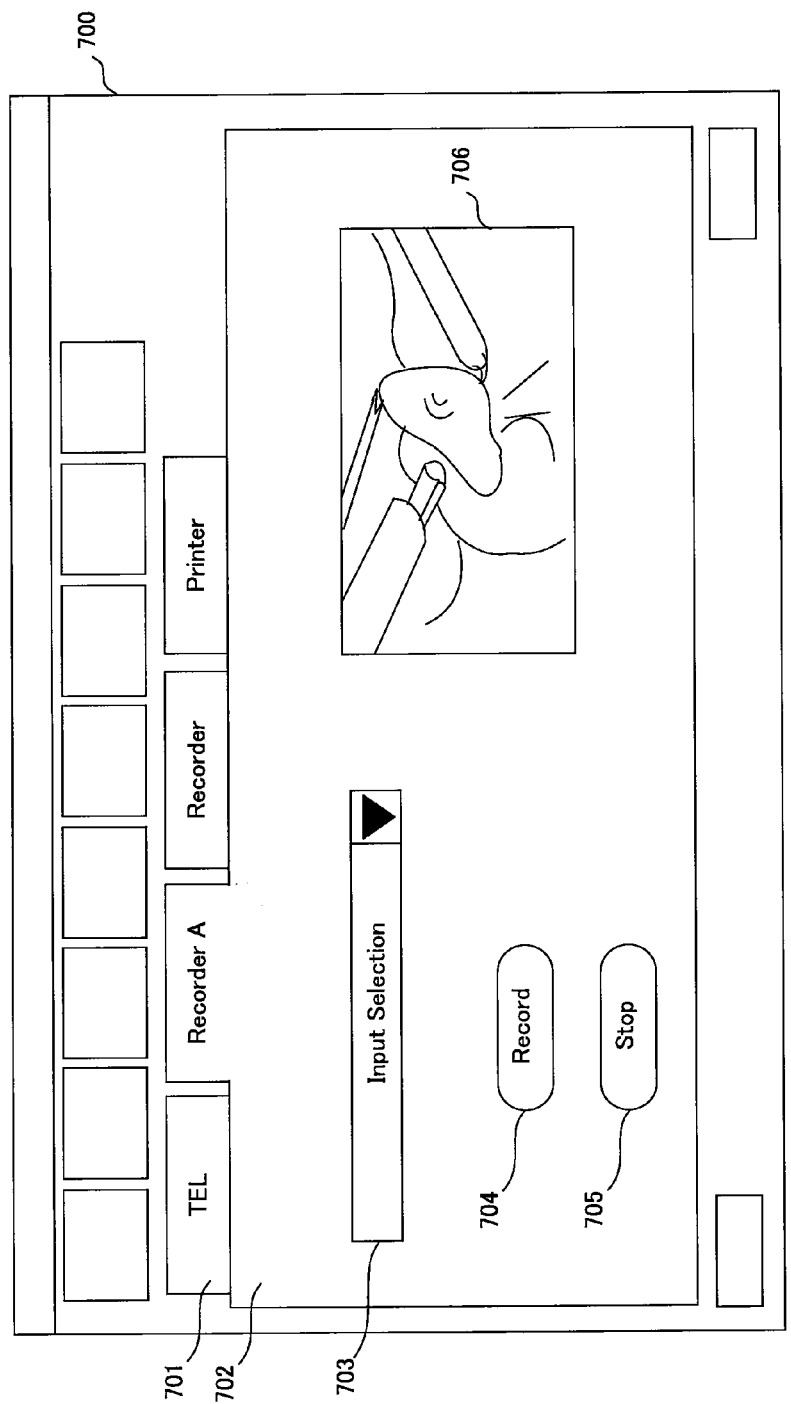
FIG. 7 shows an operation window 700 for device A according to the present embodiment.

FIG. 7 shows an operation window 700 for device A according to the present embodiment. The operation window 700 is displayed on the TP 221. The operation window 700 includes tabs 701, a selection tab display area 702, an input video selection area 703, a record button 704, a stop button 705, and a preview area 706.

On the operation window 700, it is possible to perform operations for the device selected through the selection of the tabs 701. When one of the tabs 701 is selected, the selection tab display area 702 is displayed. In FIG. 7, the tab "Recorder A" is selected, and a selection tab display area 711 for the Recorder A is displayed. Accordingly, in the example of the operation window 700 shown in FIG. 7, it is possible to manipulate the Recorder A. Also, in the example of the present embodiment, device A is Recorder A; however, the scope of the present invention is not limited to this example, and device A can be various devices.

In the input video selection area 703, it is possible to select an input source (such as an endoscope or the like) of video signals to be output to the device selected in the tag 701.

In the preview area 706, the image selected in the input video selection area 703 is displayed. However, as will be described later, when looping back is set in the setting window shown in FIG. 6, the signals of the image displayed in the preview area 706 are not the video signals output from the input source to the TP 221 via the NMC 202, but the video signals via device A.

When the record button 704 is pressed, the image displayed in the preview area is recorded on the device selected via the tabs 701. In this case, the image can be recorded on the "Recorder A". When a stop button 705 is pressed, it is possible to stop the recording operation.

Figure 8:
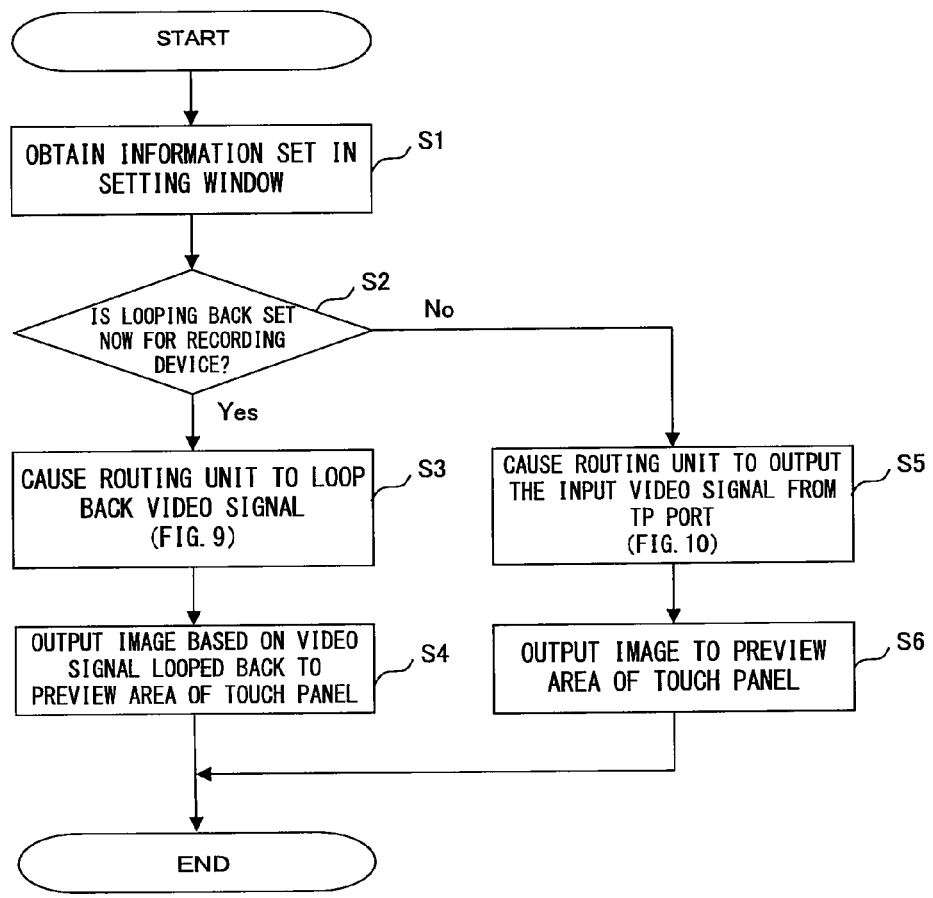
FIG. 8 is a process flow for a control unit based on the loop-back setting according to the present embodiment.

FIG. 8 is a process flow for the control unit based on the loop-back setting according to the present embodiment. When the tab 701 and the input video selection unit 703 are selected on the operation window 700, the control unit 300 executes the processes in the flowchart shown in FIG. 8.

First, using the tab "Recorder A" selected in the operation window 700 as the key, the control unit 300 searches for the setting information for device A, which is the manipulation target device, from among information set in the communication port setting window 600 stored in the storage device 306, and reads the setting information (S1).

Next, on the basis of the read setting information about device A, the control unit 300 determines whether or not looping back is set for device A (S2).

When it is found that looping back is set in S2 (Yes in S2), the control unit 300 causes the routing unit 304 to perform routing of video signals, and causes the video signals to loop back (S3). This will be explained in FIG. 9.

Figure 9:
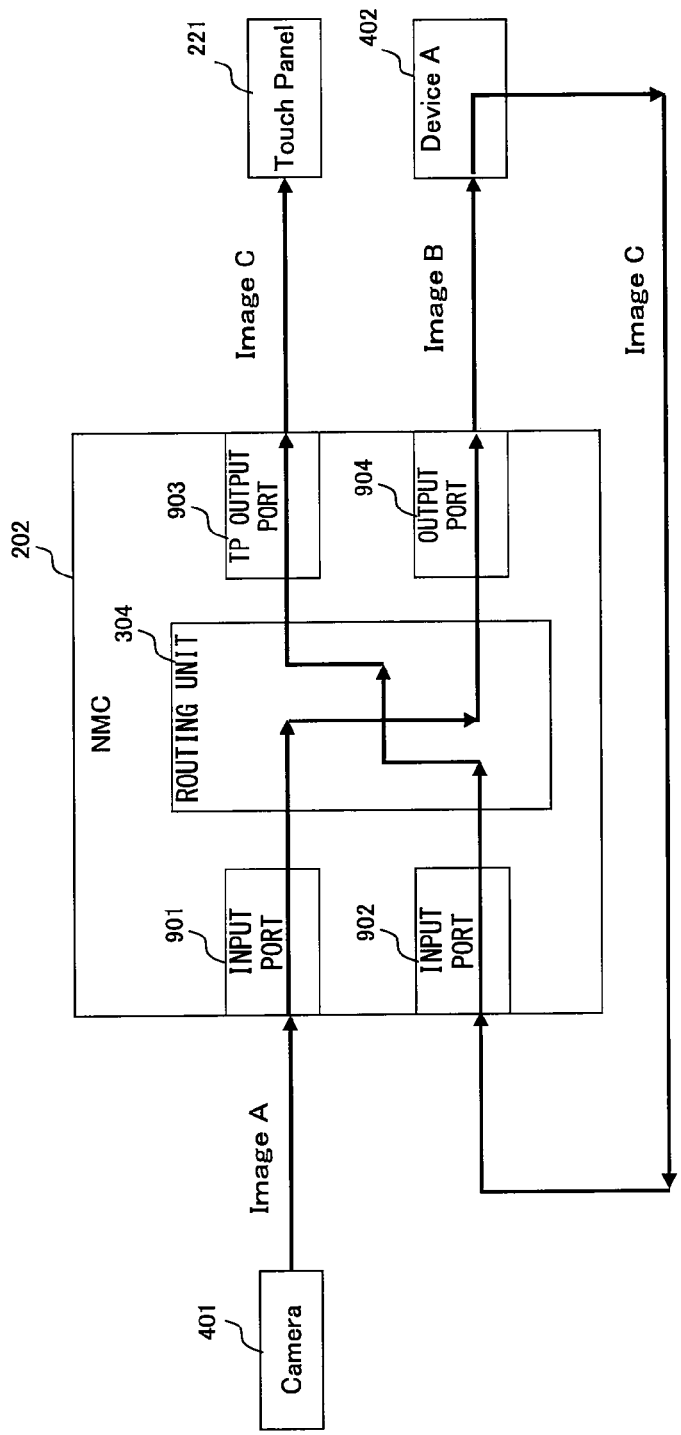
FIG. 9 is a flowchart for the video signals when looping back is set according to the present embodiment.

FIG. 9 is a flowchart for the video signals when looping back is set according to the present embodiment. The image signal (image A) output from the camera head of the endoscope (camera 401) is input into the NMC 202 via an input port 901. In accordance with instructions from the control unit 300, the routing unit 304 performs routing of image A, and outputs it as image B via an output port 904. Device A (402) outputs, as image C, the input image B. Image C is input into the NMC 202 again via the input port 902. The routing unit 304 outputs, to a TP output port 903, image C from the input port 902.

As a result of this, image C output from the TP output port 903 is output to the TP 221, and image C is displayed in the preview area 706 (S4). In other words, the image based on the looped-back video signals is output to the preview area 706 of the TP 221.

When looping back is not set in S2, the control unit 300 outputs the input video signals via the TP output port 903 (S5). This will be explained in FIG. 10.

Figure 10:
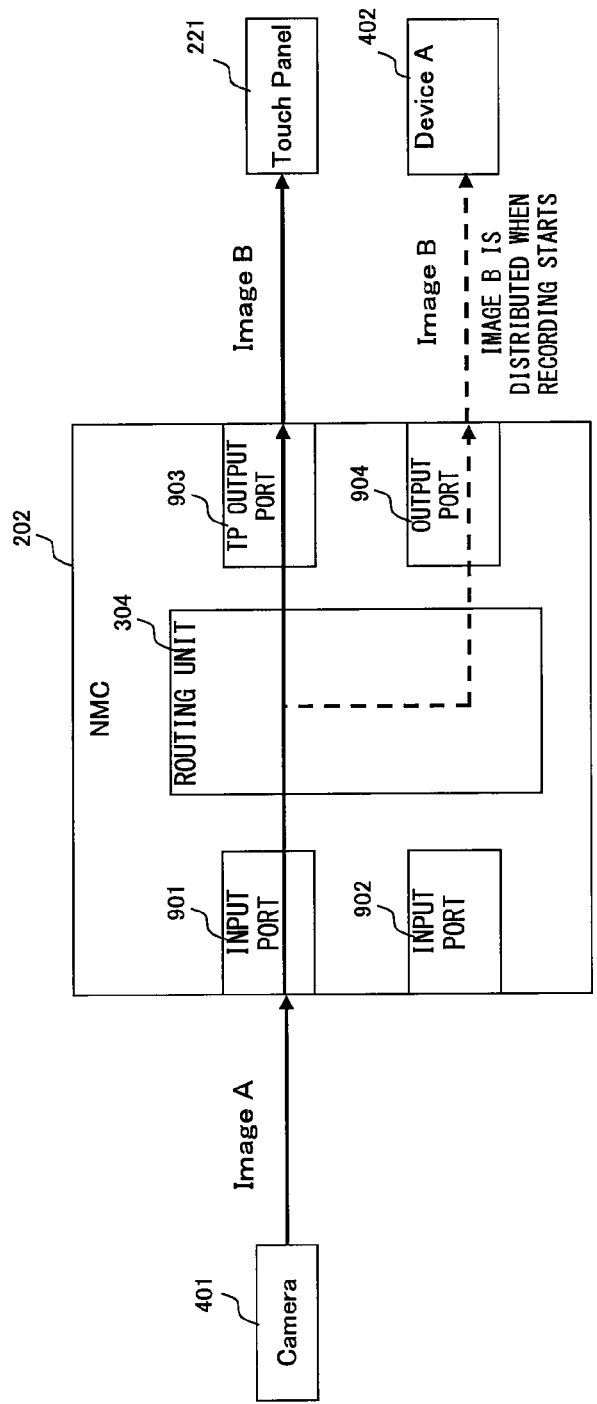
FIG. 10 is a flowchart for the video signals when looping back is not set according to the present embodiment.

FIG. 10 is a flowchart for the video signals when looping back is not set according to the present embodiment. The image signals (image A) output from the camera head of the endoscope (camera 401) is input into the NMC 202 via the input port 901. In accordance with instructions from the control unit 300, the routing unit 304 performs routing of image A, and outputs it as image B via the TP output port 903.

As a result of this, image B output from a TP output port 113 is output to the TP 221, and image B is displayed in the preview area 706 (S6). When a recording operation starts with the "record" button being pressed, the routing unit 304 distributes image B to device A. Also, it is possible to display the image before the recording operation starts.

Accordingly, when looping back is set, the image displayed in the preview area of the TP 221 is an image that has passed through device A. Accordingly, the image signal is unerringly output to device A. Accordingly, when a recording operation starts, the image can be unerringly recorded on device A.

According to the present embodiment, the medical support control system includes the recording device (for example, device A), the medical support control device (NMC 202), and the display manipulation device (TP 221). The recording device records image signals output from medical devices. The medical support control device receives image signals output from at least one of the medical devices. The medical support control device outputs the input image signals to the recording device and records them, and causes the image signals recorded in the recording device to be input again into the medical control devices. The medical control devices can synthesize the images based on the image signals with a prescribed graphical user interface (GUI).

The display manipulation device can display the GUI containing the synthesized image. Also, the display manipulation device can input information to the GUI.

In this configuration, the medical support control device can create a prescribed GUI, and can cause the GUI to be displayed as the manipulator window (for example, the operation window 700) on the basis of the input of the setting information for the recording device in the administrator setting window (setting window 600) displayed on the display manipulation device. The manipulator window includes device selection means (such as the tabs 700) for selecting one of the medical devices, image selection means (such as the input video selection unit 703) for selecting one of the image signals to be output from the medical device, and display means (such as the preview area 706) for displaying the image corresponding to the selected image signals.

Conventionally, an image to be stored is displayed on a preview window in the TP 221 and confirmed; thereafter the previewed video signals are output to the recording device in order to be recorded. However, when a cable between the NMC and the recording device is disconnected, it is not possible to record the video signals on the recording device even when the preview window is displayed.

However, according to the present embodiment, on the basis of the loop-back information set in advance, the video signals input into the NMC 202 are output to the TP 221 via the recording device. Thereby, when an image is displayed on the preview area 706 of the TP 221, there is no disorder such as disconnection or the like of the cable connecting the NMC and the storage device; accordingly, when a recording operation is performed in that case, the image can be unerringly recorded on the recording device.

Also, in the conventional techniques, confirmation of a plurality of windows is required in order to confirm functions of a plurality of devices. Accordingly, operations have been very complicated. However, according to the present embodiment, it is possible to display settings regarding the output on one manipulation window in a concentrated manner. As a result of this, operators only have to arbitrarily select devices from among input sources and output devices set in advance, which simplifies the operations.

Additionally, the scope of the present invention is not limited to any of the above embodiments, and various other configurations and embodiments are allowed without departing from the spirit of the present invention.

As described above, it is possible to provide the medical support control device for controlling medical devices and non-medical devices.

What is claimed is:

1. A medical support control system comprising:

one or more imaging devices for imaging an affected area;

one or more recording devices for recording an image signal output from the imaging devices;

a medical support control device in which the image signal output from the imaging devices is input, the medical support control device having a controlling unit for recording the input image signal on one of the recording devices and for synthesizing an image based on the image signal and a prescribed graphical user interface (GUI) when the image signal recorded on one of the recording devices is input; and a display manipulation device in which the GUI containing the synthesized image is displayed and input is possible to the GUI, wherein, on the basis of an input of setting information about the recording devices on an administrator setting window of a GUI displayed by the display manipulation device, the controlling unit creates a GUI including a device selection part for causing one of the recording devices to be selected, an image selection part for causing one of image signals output from the imaging devices to be selected, and a display part for causing the image corresponding to the selected image signal to be displayed, and causes the created GUI to be displayed on the display manipulation device as a manipulator window, and the medical support control device further comprises:

first and second image signal input units;

first and second image signal output units;

a storage unit for storing setting information about the recording device input into the administrator setting window; and a routing unit for outputting an image signal from the first or second image signal input unit to the first or second image signal output unit, on the basis of the setting information, and the selected recording device and the selected image signal, and wherein;

the first image signal input unit is connected to the imaging devices;

the first image signal output unit is connected to an image signal input unit of the display manipulation device;

the second image signal output unit is connected to an image signal input unit of the recording devices;

the second image signal input unit is connected to an image signal output unit of the recording devices; and if the setting information is set, the routing unit outputs an image signal input from the first image signal input unit to the second image signal output unit, and outputs to the first image signal output unit the image signal input from the second image signal input unit and returned via the selected recording device.

* * * * *